United States Patent [19]

Terranova et al.

[11] Patent Number: 5,466,694

[45] Date of Patent: Nov. 14, 1995

[54] COMPOSITIONS FOR SLOWING DOWN HAIR LOSS AND FOR INDUCING AND STIMULATING ITS GROWTH, BASED ON 2,4-DIAMINO-PYRIMIDINE 3-OXIDE DERIVATIVES, AND NEW 2,4-DIAMINOPYRIMIDINE 3-OXIDE DERIVATIVES

[75] Inventors: Eric Terranova, Asniéres; Jean B. Galey; Michel Hocquaux, both of Paris; Jean Maignan, Tremblay-les-Gonesse; Rémy Tuloup, Miniac-sous-Bécheral, all of France

[73] Assignee: L'Oreal, Paris, France

[21] Appl. No.: 912,512

[22] Filed: Jul. 13, 1992

[30] Foreign Application Priority Data

Jul. 11, 1991 [FR] France ................... 91 08764

[51] Int. Cl.⁶ ................ A61K 9/10; A61K 9/06
[52] U.S. Cl. ............... 514/272; 424/45; 424/DIG. 1; 424/443; 424/450; 514/937; 514/944; 514/945; 514/969; 514/880
[58] Field of Search ............... 424/45, 70, 443, 424/450, 59, 78.02, DIG. 1, 443, 450; 540/481; 514/937, 944, 945, 272, 944, 945, 969, 880

[56] References Cited

U.S. PATENT DOCUMENTS

| | | | |
|---|---|---|---|
| 3,382,248 | 5/1968 | Anthony et al. | 540/481 |
| 3,637,697 | 1/1972 | Anthony et al. | 540/481 |
| 4,820,512 | 4/1989 | Grollier | 514/256 |
| 4,973,474 | 11/1990 | Hocquaux et al. | 514/272 |
| 5,132,106 | 7/1992 | Tuloup et al. | 514/272 |

FOREIGN PATENT DOCUMENTS

| | | |
|---|---|---|
| 356271 | 7/1989 | European Pat. Off. |
| 1695959 | 10/1966 | Germany |

OTHER PUBLICATIONS

Chemical Abstracts, vol. 92, 1980, p. 696.

Primary Examiner—Raj Bawa
Attorney, Agent, or Firm—Jacobson, Price, Holman & Stern

[57] ABSTRACT

Composition for slowing down hair loss and inducing and stimulating its growth, comprising a compound of the following formula:

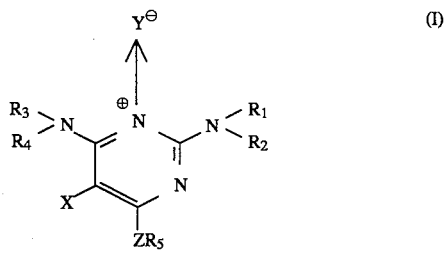

wherein $R_1$ and $R_3$ denote H; $R_2$ and $R_4$ denote H or an alkyl; $R_5$ denotes H, an alkyl, an alkenyl, a cycloalkyl, an aryl, an arylalkyl, a hydroxyalkyl or an aminoalkyl; X denotes H, halogen, alkyl, nitro, benzoyloxy or —$NHR_6$ where $R_6$ denotes H, acyl or alkyl; Z denotes sulfur or oxygen, with the proviso that Z denotes sulfur when X denotes H or $R_5$ denotes aryl; Y denotes oxygen or $OSO_3$; as well as its physiologically acceptable salts.

16 Claims, No Drawings

COMPOSITIONS FOR SLOWING DOWN HAIR LOSS AND FOR INDUCING AND STIMULATING ITS GROWTH, BASED ON 2,4-DIAMINO-PYRIMIDINE 3-OXIDE DERIVATIVES, AND NEW 2,4-DIAMINOPYRIMIDINE 3-OXIDE DERIVATIVES

The present invention relates to new compositions for slowing down hair loss and for inducing and stimulating its growth, based on 2,4-diaminopyrimidine 3-oxide derivatives, as well as to the new compounds used in these compositions.

2,4-Diamino-6-piperidinopyrimidine 3-oxide or minoxidil is already known in the state of the art for its antihypertensive qualities but also for its use in the treatment of hair loss, of pelade, of desquamative dermatitis and of alopecia.

The Applicant has discovered new compositions for the treatment and prevention of hair loss, used particularly in topical application, containing a particular family of 6-alkoxy- or 6-thioalkyl-2,4-diaminopyrimidine 3-oxide compounds which can be substituted at position 5.

The compounds retained by the Applicant are, surprisingly, very effective for hair regrowth and particularly for inducing and stimulating its growth. Additionally, they have a remarkable solubility in the media normally used in cosmetics or pharmaceuticals.

The subject of the invention is thus new compositions intended for the treatment and prevention of hair loss which contain particular 6-alkoxy- or 6-thioalkyl-2,4-diaminopyrimidine 3-oxide compounds, optionally substituted at position 5.

Another subject of the invention is new compounds used in these compositions.

Another subject of the invention is the use of these particular compounds for the preparation of a medicament intended for the therapeutic treatment of hair loss.

Other subjects will become apparent in the course of the description and examples which follow.

The compositions in accordance with the invention essentially comprise, in a physiologically acceptable medium, at least one compound corresponding to the formula (I):

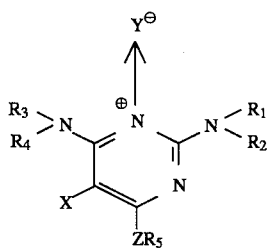

in which:

$R_1$ and $R_3$ denote a hydrogen atom;

$R_2$ and $R_4$, which are identical or different, represent a hydrogen atom or a $C_1$–$C_4$ alkyl group;

$R_5$ denotes a hydrogen atom, a $C_1$–$C_{12}$ alkyl radical, a $C_3$–$C_{12}$ alkenyl radical, a $C_3$–$C_8$ cycloalkyl radical, an aryl radical, an arylalkyl radical or a hydroxyalkyl or aminoalkyl radical in which the alkyl radical has 1 to 6 carbon atoms;

X denotes a hydrogen atom, a halogen atom, a $C_1$–$C_6$ alkyl radical, a nitro group, a benzoyloxy group or a group —$NHR_6$ in which $R_6$ denotes a hydrogen atom, an acyl radical or a $C_1$–$C_6$ alkyl radical;

Z denotes sulfur or oxygen, with the proviso that Z denotes sulfur when X denotes hydrogen or when $R_5$ denotes an aryl radical;

Y denotes oxygen or $OSO_3$;

as well as its addition salts with physiologically acceptable acids.

The halogen atoms in the structure of formula (I) are preferably chlorine, bromine, fluorine or iodine.

The $C_1$–$C_6$ alkyl radicals are preferably chosen from methyl, ethyl, propyl, n-butyl, n-pentyl and n-hexyl.

The $C_1$–$C_{12}$ alkyl radicals are preferably chosen from methyl, ethyl, propyl, 2-ethylhexyl, decyl, octyl and dodecyl.

The $C_3$–$C_{12}$ alkenyl groups are preferably chosen from allyl, n-butenyl, hexenyl and dodecenyl.

The aryl or aralkyl radicals are preferably chosen from phenyl, benzyl and tolyl.

The compounds of formula (I) according to the invention can be converted into their addition salts with pharmaceutically or cosmetically acceptable acids such as the salts of sulfuric, hydrochloric, hydrobromic, phosphoric, acetic, benzoic, salicylic, glycolic, succinic, tartaric, nicotinic, maleic, pamoic, methanesulfonic, picric and lactic acids, etc.

The compounds of general formula (I) are novel with the exception of the compound 2,4-diamino-6-hydroxy-5-bromopyrimidine 3-oxide described in the document W. L. F. Armarego and P. Waring, Aust. J. Chem., 1981, 34 (9), 1921–33 and the compound 2,4-diamino-6-thiophenylpyrimidine 3-oxide described in the document W. B. Cowden and N. W. Jacobsen, Aust. J. Chem., 1979, 32 (9), 2049–57.

The compounds in accordance with the present invention can be obtained from compounds derived from 2,4-diaminopyrimidine 3-oxide, of formula:

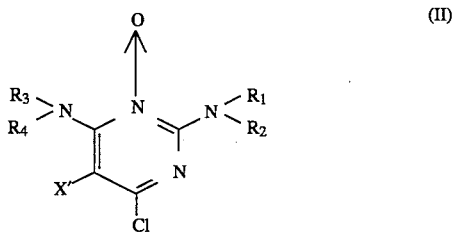

in which:

$R_1$ and $R_3$ denote a hydrogen and $R_2$ and $R_4$ denote a hydrogen or a $C_1$–$C_4$ alkyl radical and X' denotes a hydrogen or a $C_1$–$C_6$ alkyl radical or a group —$NHR_6$ where $R_6$ denotes an alkyl radical or a $C_1$–$C_6$ acyl radical.

The particular starting compounds of the following formula (IIA):

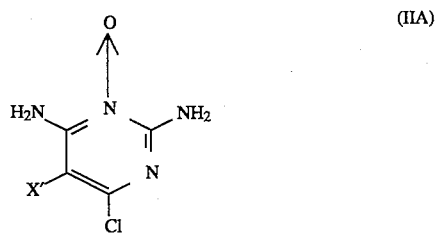

are obtained by cyclization of guanidine (1) with an alkyl cyanoacetate of the formula (2), followed by a halogenation at position 6 of the 2,4-diaminopyrimidine derivative of formula (3) obtained. An oxidation at position 3 of the pyrimidine ring is then carried out, preferably in a polar protic solvent in the presence of a percarboxylic acid R'CO$_3$H where R' denotes an alkyl or aryl radical. This process can be represented by the following scheme:

SCHEME 1

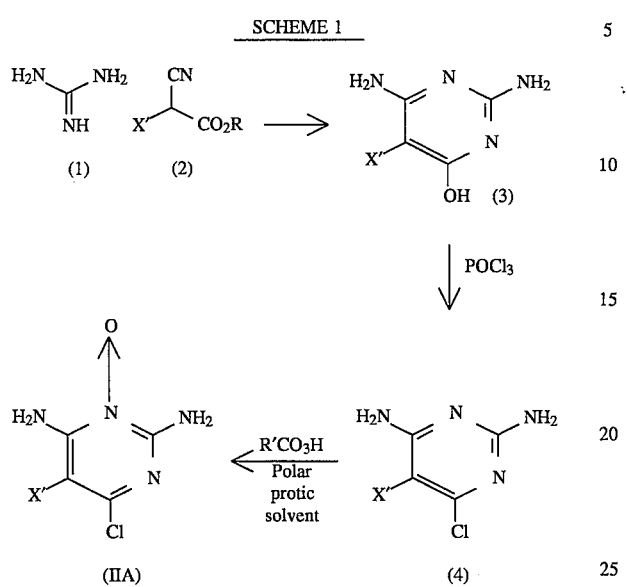

The particular starting compounds of the following formula (IIB):

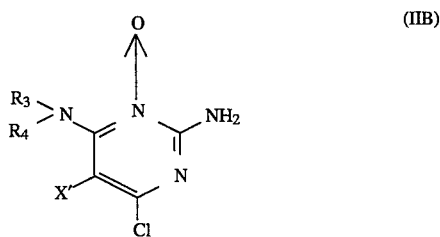

with R$_3$=H and different from R$_4$, can be obtained in a first step by cyclization of guanidine with diethyl malonate, optionally monosubstituted at the alpha-position, followed by a chlorination reaction of the pyrimidine derivative thus obtained. The amine NHR$_3$R$_4$ is then introduced by nucleophilic aromatic substitution on the pyrimidine ring of the product obtained and then an oxidation at position 3 is carried out, according to the principle described previously. This process can be represented by the following scheme:

SCHEME 2

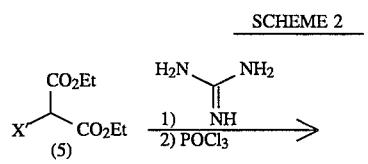

-continued
SCHEME 2

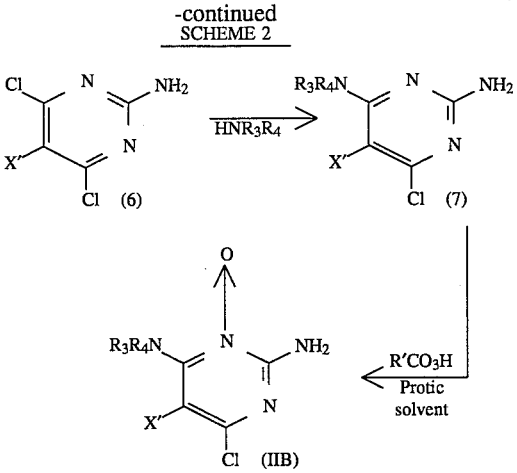

The particular starting compounds of formula (IIC):

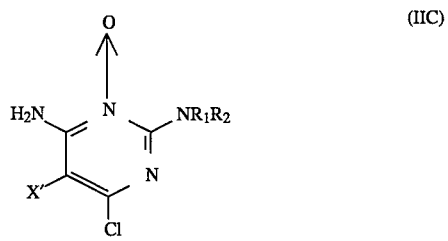

in which R$_1$ denotes hydrogen and R$_2$ denotes alkyl, are obtained by oxidation, by means of a peracid, of the pyrimidine derivative of formula:

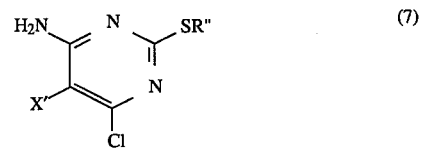

where R" denotes an aryl or an alkyl radical, followed by a nucleophilic aromatic substitution, of the group —SO$_2$R" obtained, by the amine NHR$_1$R$_2$ on the pyrimidine range. An oxidation at position 3 of the pyrimidine range is then carried out under the same conditions as previously.

The particular starting compounds of the following formula:

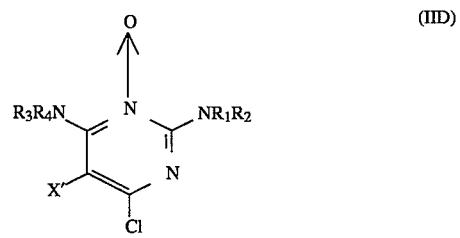

in which R$_1$ and R$_3$ denote hydrogen and R$_2$ and R$_4$ denote alkyl, can be obtained according to the following reaction scheme:

SCHEME 3

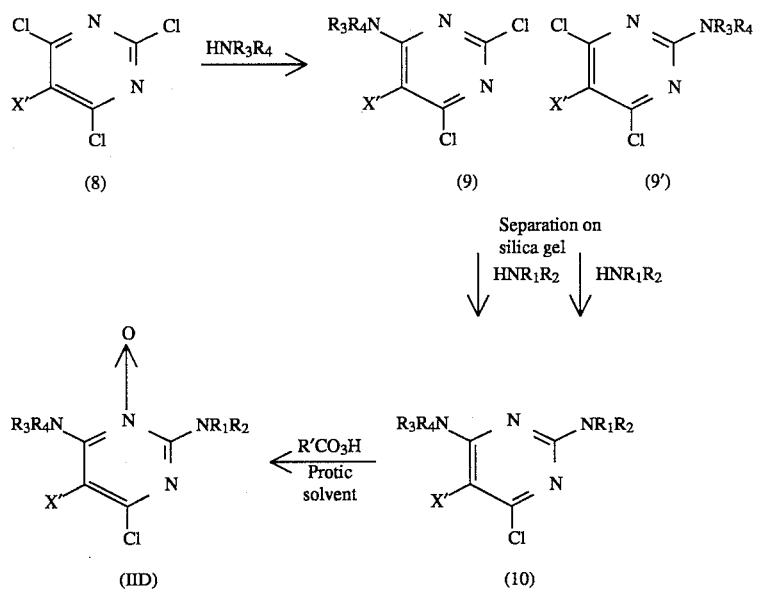

Starting from the compound of formula (8), two equivalents of the amine $NHR_3R_4$ are introduced into the pyrimidine ring and then, after separating on silica gel the products (9) and (9') formed, the second amine $NHR_1R_2$ is introduced.

An oxidation at position 3 of the pyrimidine ring is then carried out as previously.

The particular compounds of the present invention of the following formula:

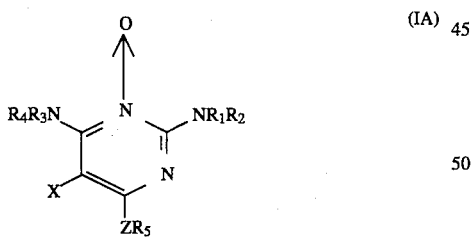

where $R_1$, $R_2$, $R_3$, $R_4$, Z and $R_5$ have the same meanings indicated above in the general formula (I), and X denotes hydrogen, a $C_1$–$C_6$ alkyl radical or a group —$NHR_6$ where $R_6$ denotes a $C_1$–$C_6$ alkyl radical or an acyl radical, can be obtained by reacting the compounds of formula (II), either with an alkoxide $W^+$ $OR_5^-$ in the corresponding alcohol $R_5OH$, where W denotes an alkali metal such as sodium, potassium or lithium, or with a thiolate $W^+$ $SR_5^-$ in the presence of a solvent such as dimethylformamide.

This process can be represented by the following reaction scheme:

SCHEME A

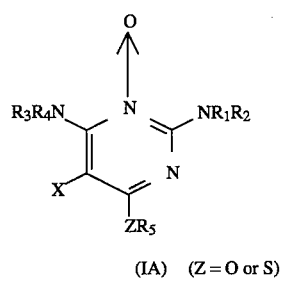

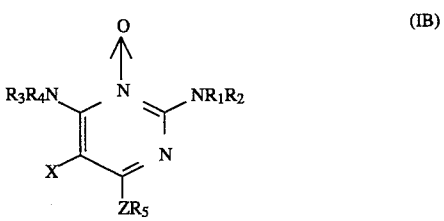

The particular compounds of the invention of the following formula:

(IB)

where $R_1$, $R_2$, $R_3$, $R_4$, $R_5$ and Z have the same meanings indicated above and X denotes a halogen atom, can be obtained by reacting a compound of formula (II) in which X' denotes hydrogen with a halogenating agent. In the case where X denotes chlorine, iodine or bromine, an N-halo-succinimide of formula (III):

(III)

for example, is used in the presence of an alcohol such as methanol.

The chlorine atom at position 6 of the pyrimidine ring is then substituted by the group —$ZR_5$ according to the process described above in Scheme A.

The process can be represented by the following scheme:

SCHEME B

The particular compounds of the invention of the following formula (IC)

can be obtained from the compounds of formula (IA) where X denotes hydrogen. An electrophilic aromatic substitution reaction is carried out using a nitrating agent, such as nitric acid, in the presence of concentrated sulfuric acid.

This process can be represented by the following reaction scheme:

SCHEME C (IA)

(IC)

The particular compounds of the invention of the following formula:

(ID)

can be obtained from the compounds of formula (IC) by catalytic reduction. Palladium on charcoal under a hydrogen atmosphere is used in particular.

This process can be represented by the following scheme:

SCHEME D (IC)    (ID)

The particular compounds of the invention of the following formula:

(IE)

can be obtained by the action of dibenzoyl peroxide in acetic acid medium on a compound of formula (IA), in which X' denotes hydrogen, according to the following reaction scheme:

SCHEME E

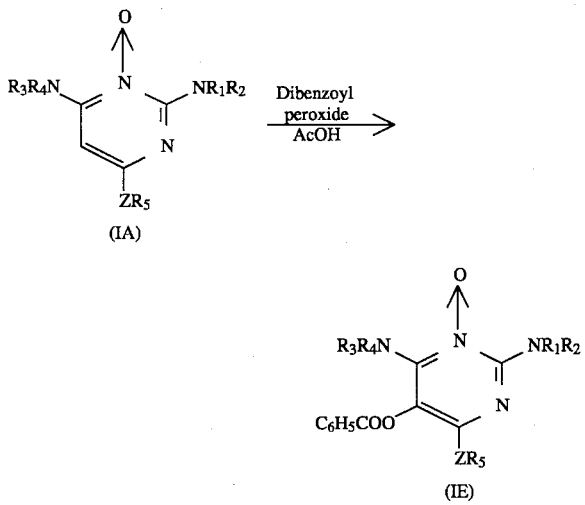

The particular compounds of the invention of general formula (I) in which Y denotes an oxygen atom can be converted into their O-sulfate homologs of formula (IF) defined below by chemical sulfating according to the conventional methods described in the literature (J. Med. Chem., 1983, 26, pages 1791–1793).

The sulfur trioxide-pyridine, sulfur trioxidetriethylamine or sulfur trioxide-ethyldiisopropylamine complexes are used as sulfating reagent.

The solvents used are preferably dimethylformamide, chloroform or acetonitrile or their binary mixtures.

The temperature is of the order of 0° to 25° C. and the reaction time varies from 1 to 24 hours.

SCHEME F

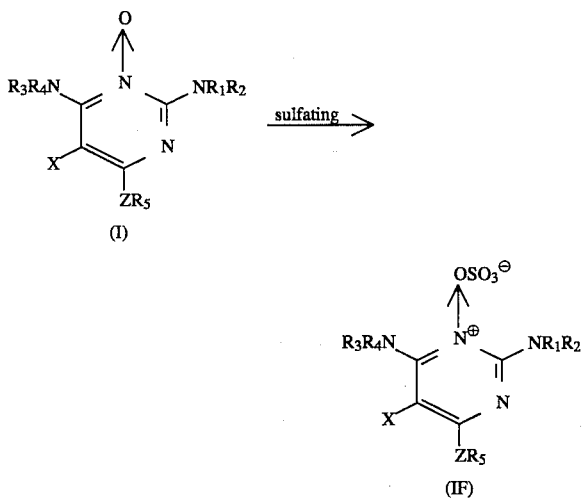

Among the compounds of the invention of general formula (I) in which Z denotes oxygen, the particularly preferred compounds are those for which $R_1$, $R_2$, $R_3$ and $R_4$ denote hydrogen, X denotes chlorine or the nitro group and $R_5$ denotes n-butyl.

Among the compounds of the invention of formula (I) in which Z denotes sulfur, the particularly preferred compounds are those for which X denotes chlorine or the nitro group, $R_1$, $R_2$, $R_3$ and $R_4$ denote a hydrogen atom and $R_5$ denotes methyl, ethyl, n-butyl, 2-hydroxyethyl, 2-aminoethyl or phenyl.

The compositions in accordance with the present invention, which contain, in a physiologically acceptable medium, at least one compound corresponding to the formula (I) or one of its addition salts with physiologically acceptable acids, can be applied in the cosmetics or pharmaceutical field, particularly in topical application. They are intended for the treatment and the prevention of hair loss, and particularly of pelade and alopecia as well as of desquamative dermatitis, and the stimulation of hair regrowth.

These compositions can contain, as physiologically acceptable medium, any medium suitable for topical application, either in cosmetics or in pharmaceuticals, and which is compatible with the active substance.

The compounds in accordance with the invention can be found in this medium contained either in the dissolved state or in the dispersed state, in particular in the micronized form.

The compositions intended to be used as pharmaceuticals are present in the form of an ointment, tincture, cream, pomade, powder, patch, impregnated pad, solution, emulsion or vesicular dispersion, lotion, gel, spray or suspension. They can be either anhydrous or aqueous according to the clinical indication.

The compounds according to the invention are present in these pharmaceutical compositions at concentrations of between 0.1 and 10% by weight, and in particular of between 0.2 and 5% by weight.

The cosmetic compositions are particularly intended to be used in the form of a lotion, gel, soap, shampoo, aerosol or foam and contain, in a cosmetically acceptable carrier, at least one compound of formula (I) or one of its addition salts with acids.

The concentration of these compounds of formula (I) in these compositions is, preferably, of between 0.01 and 5% by weight and in particular between 0.05 and 3% by weight.

The compositions in accordance with the invention can contain various additives normally used in cosmetics or in pharmaceuticals and, in particular, active substances, for example hydrating agents, such as thiamorpholine and its derivatives or urea; antiseborrheic agents such as S-carboxymethylcysteine, S-benzylcysteamine and their derivatives; and thioxolone.

The compounds in accordance with the invention can be combined with compounds which further improve their activity towards the regrowth and/or slowing down of hair loss, such as the following compounds:

nicotinic acid esters, more particularly $C_1$–$C_6$ alkyl nicotinates and particularly methyl nicotinate or benzyl nicotinate;

steroidal and nonsteroidal anti-inflammatory agents well known in the state of the art and in particular hydrocortisone, its salts and its derivatives, and niflumic acid;

retinoids and more particularly all-trans-retinoic acid, also called tretinoin, isotretinoin, retinol or vitamin A and its derivatives, such as the acetate, the palmitate or the propionate, motretinide, etretinate or zinc all-trans-retinoate;

antibacterial agents chosen more particularly from the macrolides, the pyranosides and the tetracyclines and particularly erythromycin;

calcium antagonist agents, such as, more particularly, cinnarizine and diltiazem;

hormones, such as estriol or analogs or thyroxine and its salts;

antiandrogenic agents, such as oxendolone, spironolactone or diethylstilbestrol;

OH radical scavengers, such as dimethyl sulfoxide.

It is also possible to combine with the compounds of the invention, optionally mixed with others, compounds such as diazoxide, corresponding to 3-methyl-7-chloro-[2H]-1,2,4-benzothiadiazine 1,1-dioxide; spiroxasone or 7-(acetylthio)-4',5'-dihydrospiro[androst-4-ene-17,2'-(3'H)furan]-3-one; phospholipids, such as lecithin; linoleic and linolenic acids; salicylic acid and its derivatives described in French Patent 2,581,542, and more particularly the salicylic acid derivatives which carry an alkanoyl group having 2 to 12 carbon atoms at position 5 of the benzene ring; hydroxycarboxylic or ketocarboxylic acids and their esters, lactones and their corresponding salts; anthralin or 1,8,9-trihydroxyanthracene, the carotenoids, 5,8,11,14-eicosatetraynoic or 5,8,11-eicosatriynoic acid, their esters and amides.

The compounds in accordance with the invention can also be combined with surface-active agents, particularly those chosen from the nonionic and amphoteric surface-active agents.

Among the nonionic surfactants, there are to be mentioned the polyhydroxypropyl ethers described particularly in the French Patents Nos. 1,477,048; 2,091,516; 2,169,787; 2,328,763; 2,574,786; the oxyethylenated ($C_8$-$C_9$)-alkylphenols containing 1 to 100 mol of ethylene oxide and preferably 5 to 35 mol of ethylene oxide; the alkylpolyglycosides of formula:

$C_nH_{2n+1}(C_6H_{10}O_5)_xH$      (A)

in which n varies from 8 to 15 inclusive and x from 1 to 10 inclusive.

Among the amphoteric surface-active agents, there are to be mentioned more particularly the amphocarboxyglycinates and the amphocarboxypropionates defined in the CTFA dictionary, 3rd edition, 1982, and sold, particularly, under the name Miranol® by the Miranol Company.

The compounds according to the invention can be introduced into carriers which further improve the activity as regards regrowth while, at the same time, having advantageous properties at the cosmetic level, such as volatile ternary mixtures of alkyl ethers of alkylene glycols, in particular $C_1$-$C_4$ alkyl ethers of $C_1$-$C_4$ alkylene glycols or dialkylene glycols, preferably $C_1$-$C_4$ dialkylene glycols, ethyl alcohol and water, the glycol solvent more particularly denoting ethylene glycol monoethyl ether, propylene glycol monomethyl ether or diethylene glycol monomethyl ether.

The compounds in accordance with the invention can also be introduced into gelled or thickened carriers, such as essentially aqueous carriers gelled with heterobiopolysaccharides, such as xanthan gum, scleroglucans or cellulose derivatives, aqueous-alcoholic carriers gelled with polyhydroxyethyl acrylates or methacrylates, or essentially aqueous carriers thickened in particular with polyacrylic acids crosslinked by a polyfunctional agent, such as the Carbopol products sold by the Goodrich Company.

These compositions can also contain preserving agents, stabilizing agents, pH regulating agents, agents for modifying osmetic pressure, emulsifying agents, UVA and UVB filters and antioxidant agents, such as α-tocopherol, butylhydroxyanisole or butylhydroxytoluene.

The physiologically acceptable medium can consist of water or a mixture of water and a solvent or a mixture of solvents, the solvents being chosen from the organic solvents acceptable at the cosmetic or pharmaceutical level and chosen more particularly from the lower, $C_1$-$C_4$ alcohols, such as ethyl alcohol, isopropyl alcohol or tert-butyl alcohol, the alkylene glycols or the alkyl ethers of alkylene glycol and of dialkylene glycol, such as ethylene glycol monoethyl ether, propylene glycol monomethyl ether or diethylene glycol monomethyl ether. The solvents, when they are present, are present in proportions of between 1 and 80% by weight in relation to the total weight of the composition.

The thickening agents are preferably present in proportions of between 0.1 and 5% by weight and in particular between 0.4 and 3% by weight in relation to the total weight of the composition.

Another subject of the invention is a process for cosmetic treatment of hair or of the scalp, consisting in applying to them at least one composition such as is defined above, with the aim of improving the attractiveness of the hair.

Another subject of the invention consists in the use of the composition containing the compounds of formula (I) defined above for the preparation of a medicament which has the effect of inducing or stimulating hair growth and of slowing down its loss.

The treatment principally consists in applying the composition such as is defined above to the alopecic areas of the scalp of an individual.

The preferred method of application consists in applying 1 to 2 g of the composition to the alopecic area, at a frequency of one to two applications per day, for 1 to 7 days per week for a period of 1 to 6 months.

The compositions can particularly be used in the treatment of pelade, hair loss and desquamative dermatitis.

The following examples are intended to illustrate the invention without having any limiting character.

PREPARATION EXAMPLES

EXAMPLE 1

Preparation of
2,4-Diamino-5-Chloro-6-n-Butyloxy-Pyrimidine
3-oxide

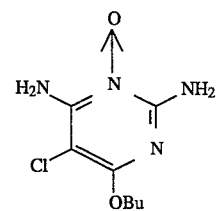

a) Preparation of 2,4-diamino-5,6-dichloropyrimidine

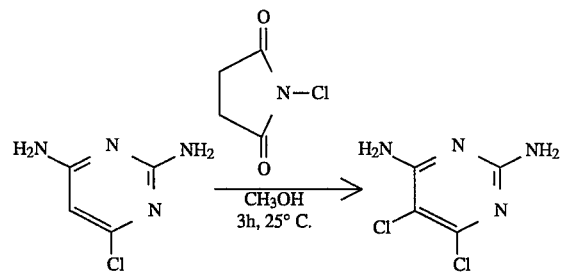

50 g of N-chlorosuccinimide are added in portions at 23° C. to a solution of 45 g of 2,4-diamino-6-chloropyrimidine in methanol (1030 ml). On completion of addition, the reaction mixture is stirred at room temperature for 3 hours. The methanol is evaporated under reduced pressure and the crude product obtained is taken up under reflux in 850 ml of water for 1 hour. After filtering, the crude product is recrystallized two times from an EtOH:H₂O (80:20) mixture to give 44.5 g of 2,4-diamino-5,6-dichloropyrimidine.

Yield =80%. MP$_K$=218° C. Elemental analysis for $C_4H_4N_4Cl_2$; M=179.

|  | C | H | N | Cl |
|---|---|---|---|---|
| Calculated | 26.82 | 2.23 | 31.28 | 39.66 |
| Found | 26.87 | 2.22 | 31.27 | 39.62 |

The ¹H NMR and mass spectra are in agreement with the expected structure.

b) Preparation of 2,4-diamino-5-chloro-6-n-butyloxypyrimidine

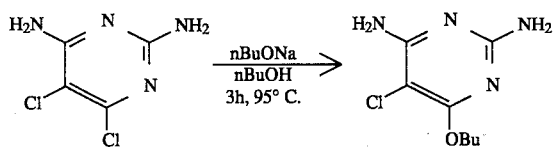

15.6 g of sodium are added to 1.3 l of n-butanol.

After the sodium has completely dissolved, 87 g of 2,4-diamino-5,6-dichloropyrimidine are added.

The mixture is heated at 95° C. for 3 hours.

After cooling the mixture, 300 ml of water are added and the mixture is stirred and separated.

The organic phase is taken to dryness.

The product obtained is recrystallized from 1 l of a water/methanol (1/1) mixture.

95.7 g of white product are obtained.

Yield: 91%. MP$_K$=135° C. Elemental analysis for $C_8H_{13}N_4OCl$ 0.1H₂O; M=218.3.

|  | C | H | N | O | Cl |
|---|---|---|---|---|---|
| Calculated | 43.98 | 6.05 | 25.65 | 8.06 | 16.26 |
| Found | 43.90 | 6.05 | 25.68 | 8.17 | 16.20 |

The ¹H NMR and mass spectra are in accordance with the expected structure.

c) Preparation of 2,4-diamino-5-chloro-6-butyloxypyrimidine 3-oxide

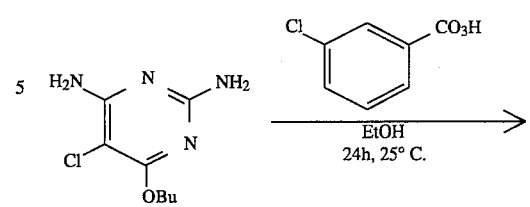

50 g of 2,4-diamino-5-chloro-6-butyloxypyrimidine are added to 1.5 l of absolute ethanol.

The solution is cooled to 5° C. and then 145 g of m-chloroperbenzoic acid (55%) are gradually added.

The mixture is left to return to room temperature and is stirred for 24 hours.

After taking the reaction mixture to dryness, 400 ml of water are added and acidification is carried out with 70 ml of concentrated hydrochloric acid.

The precipitate obtained is filtered.

The mother liquors are alkalified with 90 ml of sodium hydroxide solution, the precipitate obtained is filtered and then washed with water.

After recrystallizing from 300 ml of a water/ethanol (1/1) mixture and washing with acetone, 15 g are obtained.

Yield=28%. MP$_K$=140° C. Elemental analysis for $C_8H_{13}N_4O_2Cl$; M=232.5.

|  | C | H | N | O | Cl |
|---|---|---|---|---|---|
| Calculated | 41.29 | 5.59 | 24.09 | 13.76 | 15.27 |
| Found | 41.35 | 5.60 | 23.87 | 14.00 | 15.22 |

The ¹H NMR and mass spectra are in agreement with the expected structure.

EXAMPLE 2

Preparation of 2,4-diamino-6-thiophenylpyrimidine 3-oxide

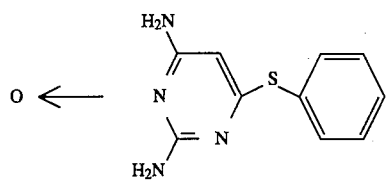

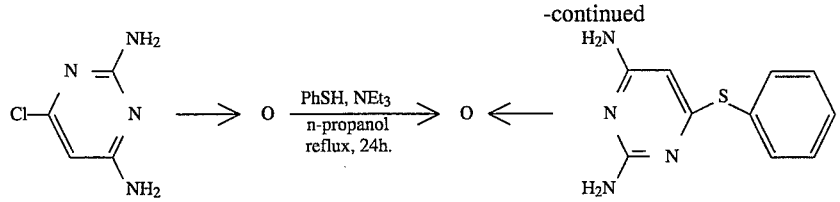

5 g of 2,4-diamino-6-chloropyrimidine 3-oxide, 6.85 g of thiophenol and 11.5 g of triethylamine are placed in 110 ml of n-propanol. The reaction mixture is heated at reflux for 24 hours. It is evaporated to dryness. The residue is taken up in 25 ml of ethyl ether, stirred for ½ an hour, filtered on sintered glass and rinsed with 2×25 ml of ethyl ether. The precipitate is taken up in 75 ml of water. The pH is adjusted to 1 with concentrated hydrochloric acid. After stirring for ½ an hour, the pH is returned to 8 by addition of concentrated sodium hydroxide solution. The precipitate is filtered, rinsed with 10 ml of water and then recrystallized twice from a 75/25 ethanol/water mixture. 3.35 g of 2,4-diamino-6-thiophenylpyrimidine 3-oxide are obtained.

Yield =46%. Melting point=decomposition from 265° C. Elemental analysis for $C_{10}H_{10}N_4OS$; M=234.

|  | C | H | N | O | S |
|---|---|---|---|---|---|
| Calculated | 51.28 | 4.27 | 23.93 | 6.84 | 13.68 |
| Found | 51.24 | 4.34 | 24.06 | 7.03 | 13.58 |

The $^1H$ NMR and mass spectra are in agreement with the expected structure.

EXAMPLE 3

Preparation of 2,4-diamino-6-thioethylpyrimidine 3-oxide

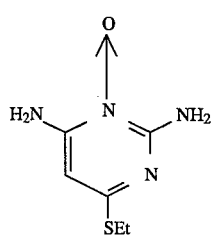

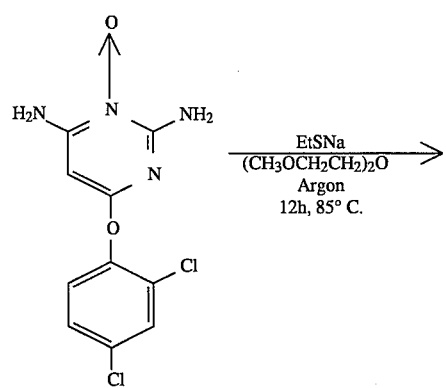

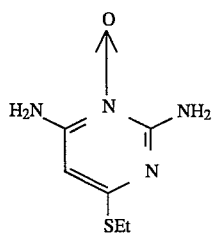

Operating method:

30 g of 2,4-diamino-6-(2',4'-dichlorophenoxy)pyrimidine 3-oxide are dissolved in 400 ml of diglyme at 85° C. and 23 g of sodium thiolate are then added in portions. The reaction mixture is stirred at 85° C. under argon for 12 hours. The solvent is evaporated and the crude product is taken up in an ethanolic hydrochloric acid solution until a pH of 2 is obtained. The precipitate is filtered (precipitate 1) and the filtrate is concentrated and taken up in diethyl ether. A solid is obtained which is combined with precipitate 1. The whole is dissolved in water and the pH is brought to 8 using a sodium hydroxide solution. The precipitate is filtered and stirred for 30 minutes in diethyl ether. After filtering, 9.6 g of 2,4-diamino-6-thioethylpyrimidine 3-oxide are obtained.

Yield =50%. Elemental analysis for $C_6H_{10}N_4OS$; M=186.

|  | C | H | N | O | S |
|---|---|---|---|---|---|
| Calculated | 38.70 | 5.37 | 30.10 | 8.60 | 17.20 |
| Found | 38.75 | 5.39 | 30.02 | 8.72 | 17.14 |

The $^1H$ NMR and mass spectra are in agreement with the expected structure.

EXAMPLE 4

Preparation of 2,4-diamino-6-thiobutylpyrimidine 3-oxide

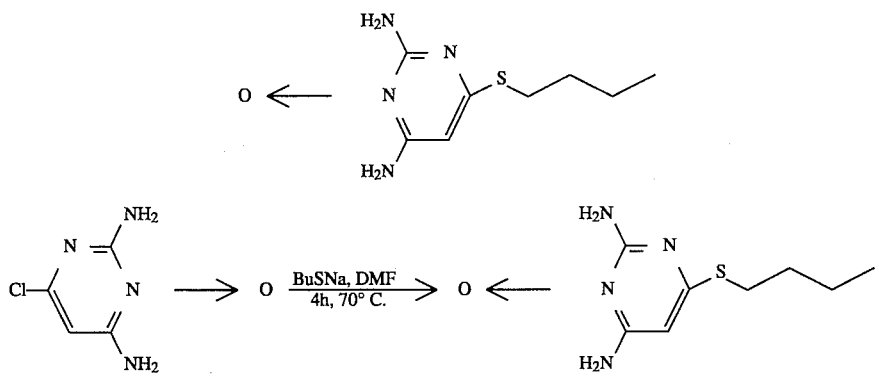

1 g of 2,4-diamino-6-chloropyrimidine 3-oxide is dissolved in 50 ml of dimethylformamide at 70° C. 1.75 g of sodium butanethiolate are added. The reaction mixture is stirred for 4 hours at 70° C. It is evaporated to dryness. The residue is taken up in 10 ml of water. The precipitate obtained is filtered on sintered glass and rinsed with 5 ml of water. It is recrystallized from 8 ml of methanol. The precipitate is rinsed with 10 ml of ethyl ether. 720 mg of 2,4-diamino-6-thiobutylpyrimidine 3-oxide are obtained.

Yield=57%. Melting point =178° C. Elemental analysis for $C_8H_{14}N_4OS$; M=214.

|  | C | H | N | O | S |
| --- | --- | --- | --- | --- | --- |
| Calculated | 44.86 | 6.54 | 26.17 | 7.47 | 14.95 |
| Found | 44.74 | 6.50 | 26.25 | 7.60 | 15.01 |

The $^1H$ NMR and mass spectra are in agreement with the expected structure.

EXAMPLE 5

Preparation of
2,4-diamino-5-chloro-6-thiobutylpyrimidine 3-oxide

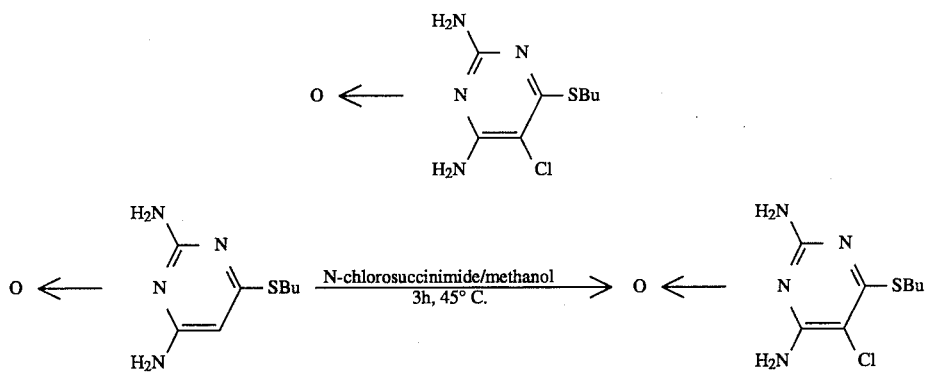

1 g of 2,4-diamino-6-thiobutylpyrimidine 3-oxide is dissolved in 100 ml of methanol. 935 mg of N-chlorosuccinimide are added. The reaction mixture is stirred at 45° C. for 3 hours and then evaporated to dryness. The residue is taken up in 2 ml of ethanolic hydrochloric acid (8.6M). 100 ml of ethyl ether are added. The white precipitate obtained is filtered on sintered glass and rinsed with 10 ml of ethyl ether. The precipitate is taken up in 5 ml of water. The pH is adjusted to 8 by addition of 10N sodium hydroxide solution. After stirring for ½ an hour, the precipitate is filtered on sintered glass, rinsed with 2×5 ml of water and dried under vacuum over phosphorus pentoxide. It is recrystallized from 10 ml of 50—50 ethanol-water. 290 mg of 2,4-diamino-5-chloro-6-thiobutylpyrimidine 3-oxide are obtained.

Yield =25%. Melting point=decomposition from 70° C. Elemental analysis for $C_8H_{13}ClN_4OS$; M=248.5.

|  | C | H | Cl | N | O | S |
| --- | --- | --- | --- | --- | --- | --- |
| Calculated | 38.63 | 5.23 | 14.28 | 22.53 | 6.44 | 12.88 |
| Found | 38.53 | 5.26 | 14.18 | 22.31 | 6.61 | 12.80 |

The $^{13}C$ NMR and mass spectra are in agreement with the expected structure.

EXAMPLE 6

Preparation of
2,4-diamino-5-nitro-6-thiobutylpyrimidine 3-oxide

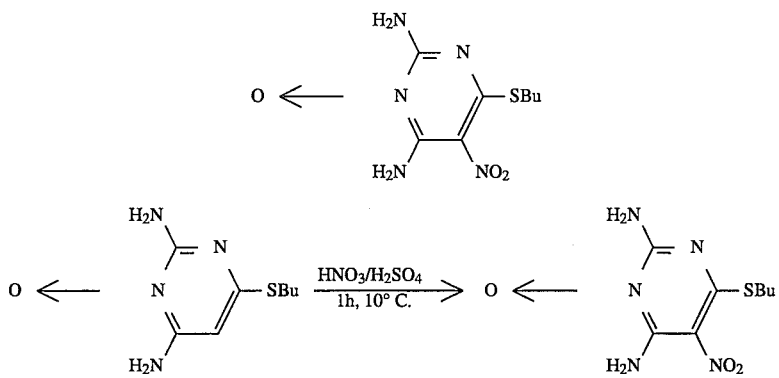

1 g of 2,4-diamino-6-thiobutylpyrimidine 3-oxide is dissolved in 10 ml of 95% sulfuric acid. The reaction mixture is cooled to 10° C. 0.4 ml of 64% nitric acid in solution in 2.5 ml of 95% sulfuric acid is added dropwise without exceeding 10° C. The mixture is stirred for 1 hour at 10° C. and is then poured onto 100 ml of iced water. After stirring for 1 hour, the precipitate is filtered on sintered glass. It is taken up in 10 ml of water. The pH is adjusted to 8 by addition of 10N sodium hydroxide solution. The orange precipitate is filtered on sintered glass, washed with 5 ml of water and dried under vacuum over phosphorus pentoxide. It is recrystallized from a 80/20 ethanol/water mixture. 450 mg of 2,4-diamino-5-nitro-6-thiobutylpyrimidine 3-oxide are obtained.

Yield =37%. Melting point =189° C. Elemental analysis for $C_8H_{13}N_5O_3S$; M=259.

|  | C | H | N | O | S |
|---|---|---|---|---|---|
| Calculated | 37.06 | 5.02 | 27.03 | 18.53 | 12.35 |
| Found | 37.07 | 5.07 | 27.09 | 18.70 | 12.29 |

The $^1H$ NMR and mass spectra are in agreement with the expected structure.

EXAMPLE 7

Preparation of 2,4-diamino-5-nitro-6-n-butyloxypyrimidine 3-oxide

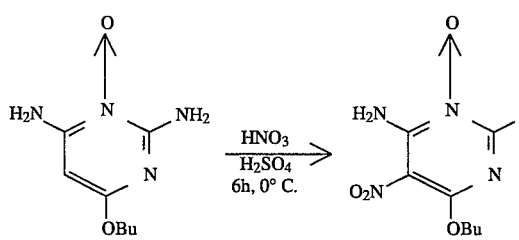

Operating method:

2.8 g of 2,4-diamino-6-n-butyloxypyrimidine 3-oxide are dissolved in 10 ml of concentrated sulfuric acid and 10 ml of a 65% $HNO_3$ and concentrated $H_2SO_4$ mixture in the proportions $HNO_3 : H_2SO_4=1:4$ are then added dropwise and at a temperature of less than +5° C. The solution is stirred for 6 hours at 0° C.

The reaction mixture is poured onto 250 g of crushed ice and neutralized by addition of 35 g of KOH pellets and then with 15 g of $KHCO_3$. The mixture is filtered on sintered glass and the precipitate is washed with water. The green-yellow solid obtained is recrystallized from a 1:5 $H_2O$/ethanol mixture. 0.5 g of 2,4-diamino-5-nitro-6-n-butyloxypyrimidine 3-oxide is obtained.

Yield =14%. Elemental analysis for $C_8H_{13}N_5O_3 0.5 H_2O$; MW=252.

|  | C | H | N | O |
|---|---|---|---|---|
| Calculated | 38.24 | 5.57 | 27.89 | 28.68 |
| Found | 37.83 | 5.32 | 27.43 | 28.22 |

The $^{13}C$ NMR and mass spectra are in agreement with the expected structure.

EXAMPLE 8

Preparation of 2,4-diamino-6-thiomethylpyrimidine 3-oxide

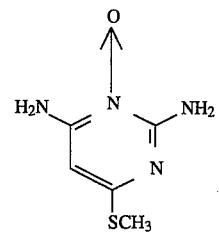

Operating method:

To a solution of 70 cm³ of absolute ethanol, containing one sodium hydroxide pellet and degassed beforehand with argon, are added 7 g of 6-chloro-2,4-diaminopyrimidine 3-oxide. After dissolving, 4.58 g of sodium methanethiolate are added in small portions. The reaction mixture is heated under reflux for 5 hours and is then filtered on sintered glass at room temperature. The precipitate obtained is washed with water and is dried under vacuum.

Yield =80%. Melting point =276° C. Elemental analysis for $C_5H_8N_4OS$; MW=172.

|  | C | H | N | O | S |
|---|---|---|---|---|---|
| Calculated | 34.87 | 4.68 | 33.53 | 9.29 | 18.62 |
| Found | 34.80 | 4.69 | 32.55 | 9.38 | 18.65 |

The $^1$H NMR and mass spectra are in agreement with the expected structure.

EXAMPLE 9

Preparation of 6-(β-aminoethylthio)-2,4-diaminopyrimidine 3-oxide

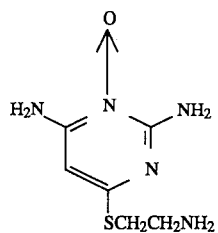

Operating method:

To a solution of 1 liter of absolute methanol, containing 31.2 g of cysteamine hydrochloride and degassed beforehand with argon, are added 29.7 g of sodium methoxide so that the temperature is best below or equal to 30° C. The reaction mixture is heated under reflux and then 40 g of 6-chloro-2,4-diaminopyrimidine 3-oxide are added in small portions. The reaction mixture is heated under reflux for 10 hours and is then filtered while hot. The filtrate is evaporated under vacuum and is then purified on a silica column in dichloromethane while progressively increasing the polarity with methanol. The pure fractions are evaporated under vacuum and the residue is recrystallized from the minimum amount of boiling ethanol. 15 g of offwhite powder are obtained.

Yield =30%. Melting point =212° C. Elemental analysis for $C_6H_{11}N_5OS$; MW=201.

|  | C | H | N |
|---|---|---|---|
| Calculated | 35.81 | 5.51 | 34.80 |
| Found | 35.37 | 5.34 | 34.04 |

The $^1$H NMR and mass spectra are in agreement with the expected structure.

EXAMPLE 10

Preparation of 6-(β-hydroxyethylthio)-2,4-diamino-pyrimidine 3-oxide

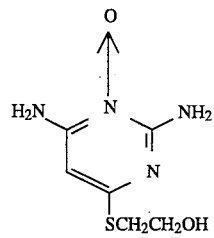

Operating method:

To a solution of 200 cm$^3$ of absolute methanol, Containing 8.8 cm$^3$ of mercaptoethanol and degassed beforehand with argon, are added 6.8 g of sodium methoxide so that the temperature is kept below or equal to 30° C. The reaction mixture is heated under reflux and then 20 g of 6-chloro-2,4-diaminopyrimidine 3-oxide are added in small portions. The reaction mixture is heated for 2×8 hours under reflux and is then filtered on sintered glass at room temperature. The precipitate obtained is washed with water, dried under vacuum and then recrystallized from the minimum amount of dimethyl sulfoxide heated to a temperature of 150° C. 12 g of white powder are obtained.

Yield =50%. Melting point =245° C. Elemental analysis for $C_6H_{10}N_4O_2S$ 0.25 $H_2O$; MW =206.7.

|  | C | H | N | O | S |
|---|---|---|---|---|---|
| Calculated | 34.86 | 5.12 | 27.10 | 17.41 | 15.51 |
| Found | 34.40 | 5.34 | 26.71 | 16.90 | 15.76 |

The $^1$H NMR and mass spectra are in agreement with the expected structure.

EXAMPLE 11

Preparation of 2-amino-4-isobutylamino-5-chloro-6-ethoxy-pyrimidine 3-oxide

Stage 1: 2-amino-4-isobutylamino-6-chloropyrimidine.

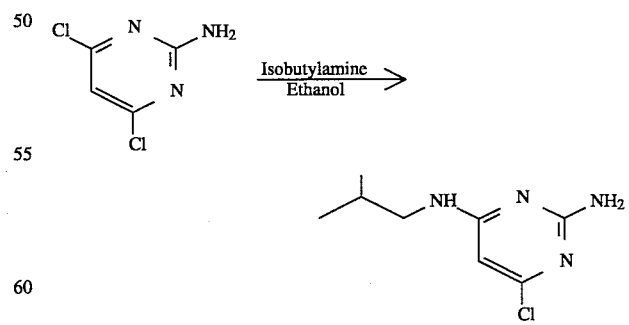

50 g of 2-amino-4,6-dichloropyrimidine are suspended in 250 ml of ethanol. 45.65 g of isobutylamine are added. The reaction mixture is heated under reflux for 3 hours. It is evaporated to dryness. The oily residue is taken up in 250 ml of water. The mixture is stirred vigorously for 1 hour. The precipitate formed is filtered on sintered glass, washed with 100 ml of water and then dried under vacuum over phosphorus pentoxide. It is recrystallized from 500 ml of isopropyl ether. 50.15 g of 2-amino-4-isobutylamino-6-chloropyrimidine are obtained.

Yield =82%.

The mass spectrum is in agreement with the expected structure.

Stage 2: 2-amino-4-isobutylamino-6-chloropyrimidine 3-oxide.

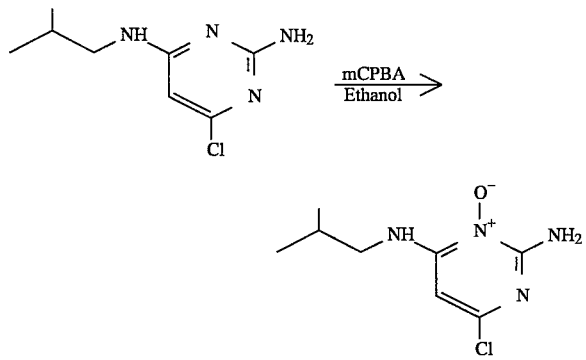

34.70 g of 2-amino-4-isobutylamino-6-chloropyrimidine are dissolved in 250 ml of ethanol. 81.50 g of metachloroperbenzoic acid, in solution in 350 ml of ethanol, are added dropwise and while keeping the temperature of the reaction mixture at 20° C. After stirring for 2 h 30 min, the precipitate formed is filtered on sintered glass, washed with 100 ml of ethyl ether and then taken up in 100 ml of water. The pH is adjusted to 8 by addition of concentrated sodium hydroxide solution. After stirring for 1 hour, the precipitate is filtered on sintered glass, washed with 3×50 ml of water and dried under vacuum over phosphorus pentoxide at 50° C. 11.30 g of 2-amino-4-isobutylamino-6-chloropyrimidine 3-oxide are obtained.

Yield =30%. Elemental analysis for $C_8H_{13}N_4OCl$: M=216.5.

|  | C | H | N | O | Cl |
| --- | --- | --- | --- | --- | --- |
| Calculated | 44.34 | 6.00 | 25.87 | 7.39 | 16.40 |
| Found | 44.52 | 5.96 | 25.75 | 7.46 | 16.41 |

The mass spectrum is in agreement with the expected structure.

Stage 3: 2-amino-4-isobutylamino-5,6-dichloropyrimidine 3-oxide.

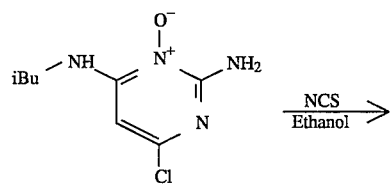

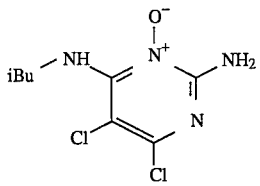

6.30 g of 2-amino-4-isobutylamino-6-chloropyrimidine 3-oxide are suspended in 110 ml of ethanol. 4.85 g of N-chlorosuccinimide are added. The reaction mixture is heated under reflux for 2 hours and then evaporated to dryness. The residue is taken up in 50 ml of water. The pH is adjusted to 8 by addition of concentrated sodium hydroxide solution. The precipitate formed is filtered on sintered glass, washed with water until neutral and dried under vacuum over phosphorus pentoxide. It is recrystallized from 150 ml of ethanol. 4.30 g of 2-amino-4-isobutylamino-5,6-dichloropyrimidine 3-oxide are obtained.

Yield =59%. Elemental analysis for $C_8H_{12}N_4OCl_2$; M=251.

|  | C | H | N | O | Cl |
| --- | --- | --- | --- | --- | --- |
| Calculated | 38.25 | 4.78 | 22.31 | 6.38 | 28.29 |
| Found | 38.37 | 4.81 | 22.26 | 6.53 | 28.29 |

The mass spectrum is in agreement with the expected structure.

Stage 4: 2-amino-4-isobutylamino-5-chloro-6-ethoxypyrimidine 3-oxide.

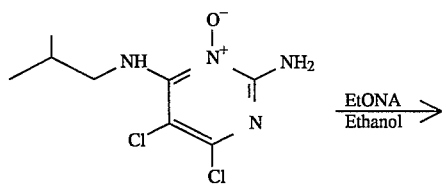

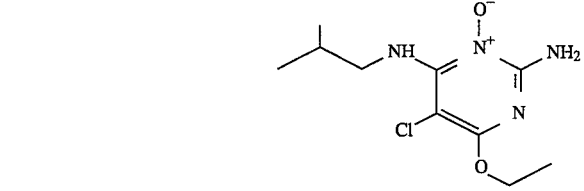

400 mg of sodium are dissolved in 30 ml of ethanol while bubbling with argon. 3 g of 2-amino-4-isobutylamino-5,6-dichloropyrimidine 3-oxide are added in small portions using a spatula. The reaction mixture is heated under reflux for 2 hours and is then evaporated to dryness. The residue is taken up in 10 ml of water. After stirring for 1 hour, the precipitate formed is filtered on sintered glass, washed with 3×10 ml of water and dried under vacuum over phosphorus pentoxide. It is recrystallized from 10 ml of acetonitrile. 2.40 g of 2-amino-4-isobutylamino-5-chloro-6-ethoxypyrimidine 3-oxide are obtained.

Yield =77%. Elemental analysis for $C_{10}H_{17}N_4O_2Cl$; M=260.5.

| | C | H | N | O | Cl |
|---|---|---|---|---|---|
| Calculated | 46.07 | 6.52 | 21.50 | 12.28 | 13.63 |
| Found | 46.19 | 6.61 | 21.63 | 12.27 | 13.48 |

The $^1$H NMR and mass spectra are in agreement with the expected structure.

EXAMPLE 12

Preparation of 2-amino-4-isobutylamino-5-chloro-6-thiomethylpyrimidine 3-oxide

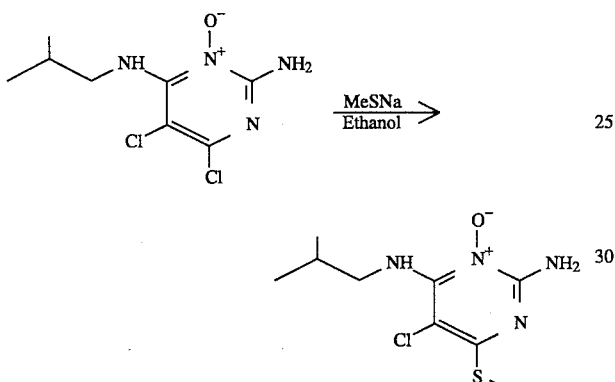

Operating method:

2.5 g of 2-amino-4-isobutylamino-5,6-dichloropyrimidine 3-oxide, prepared according to the first 3 stages of the preparation process of Example 11, are suspended in 25 ml of ethanol. 800 mg of sodium methanethiolate are added. The reaction mixture is heated under reflux for 5 hours and is then evaporated to dryness. The residue is taken up in 20 ml of water. The pH is adjusted to 1 by addition of concentrated hydrochloric acid. After stirring for ½ hour, the precipitate formed is filtered on sintered glass and then taken up in 10 ml of water. The pH is adjusted to 8 by addition of concentrated sodium hydroxide solution. The solution is extracted with 2×20 ml of ethyl acetate. The organic phase is dried over sodium sulfate and evaporated to dryness. The residue is recrystallized from 17 ml of an isopropyl ether 9/acetone 1 mixture. 1 g of 2-amino-4-isobutyl-amino-5-chloro-6-thiomethylpyrimidine 3-oxide is obtained.

Yield =38%. Elemental analysis for $C_9H_{15}N_4OSCl$; M=262.5.

| | C | H | N | O | S | Cl |
|---|---|---|---|---|---|---|
| Calculated | 41.14 | 5.71 | 21.33 | 6.09 | 12.19 | 13.52 |
| Found | 41.18 | 5.74 | 21.33 | 6.29 | 12.25 | 13.62 |

The $^1$H NMR and mass spectra are in agreement with the expected structure.

FORMULATION EXAMPLES

Example 1

Hair Lotion

| | |
|---|---|
| 2,4-Diamino-5-chloro-6-butyloxy-pyrimidine 3-oxide | 1.5 g |
| Absolute ethanol | 92.3 g |
| Propylene glycol | 6.2 g |

Example 2

Lotion

| | |
|---|---|
| 2,4-Diamino-6-thiophenyl-pyrimidine 3-oxide | 0.40 g |
| Absolute ethanol | 93.3 g |
| Propylene glycol | 6.3 g |

Example 3

Lotion

| | |
|---|---|
| 2,4-Diamino-5-chloro-6-butyloxy-pyrimidine 3-oxide | 0.9 g |
| Propylene glycol | 22.6 g |
| Ethanol | 43.9 g |
| Water qs | 100.0 g |

Example 4

Lotion

| | |
|---|---|
| 2,4-Diamino-6-thiophenylpyrimidine-3-oxide | 0.9 g |
| Propylene glycol | 22.6 g |
| Ethanol | 43.9 g |
| Water qs | 100.0 g |

These compositions are applied to the alopecic areas of the scalp at the rate of once per day for 4 months.

We claim:

1. A composition for slowing down hair loss and for inducing and stimulating its growth, which comprises, in a physiologically acceptable medium, between 0.1 and 10% by weight relative to the total weight of the composition of at least one compound corresponding to the following formula:

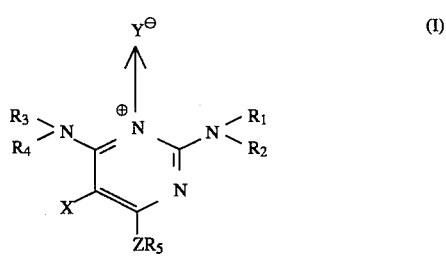

in which:

$R_1$ and $R_3$ denote a hydrogen atom;

$R_2$ and $R_4$, which are identical or different, represent a hydrogen atom or a $C_1$–$C_4$ alkyl group;

$R_5$ denotes a hydrogen atom, a $C_1$–$C_{12}$ alkyl radical, a $C_3$–$C_{12}$ alkenyl radical, a $C_3$–$C_8$ cycloalkyl radical, an aryl radical, an arylalkyl radical or a hydroxyalkyl or aminoalkyl radical in which the alkyl radical has 1 to 6 carbon atoms;

X denotes a hydrogen atom, a halogen atom, a $C_1$–$C_6$ alkyl radical, a nitro group, a benzoyloxy group or a group —$NHR_6$ in which $R_6$ denotes a hydrogen atom, an acyl radical or a $C_1$–$C_6$ alkyl radical;

Z denotes sulfur or oxygen, with the proviso that Z denotes sulfur when X denotes hydrogen or when $R_5$ denotes an aryl radical;

Y denotes oxygen or $OSO_3$; as well as its addition salts with physiologically acceptable acids.

2. The composition as claimed in claim 1, wherein, in formula (I), the $C_1$–$C_6$ alkyl radicals are methyl, ethyl, propyl, n-butyl, n-pentyl or n-hexyl; the $C_1$–$C_{12}$ alkyl radicals are methyl, ethyl, propyl, n-butyl, n-pentyl, n-hexyl, 2-ethylhexyl, octyl, decyl or are dodecyl; the $C_3$–$C_{12}$ alkenyl groups are allyl, butenyl, hexenyl, decenyl or dodecenyl; the aryl radicals are phenyl or benzyl; and the halogen atoms are chlorine, bromine, fluorine or iodine.

3. The composition as claimed in claim 1, wherein in the compound of formula (I) Z denotes sulfur; X denotes chlorine or nitro; $R_1$, $R_2$, $R_3$ and $R_4$ denote hydrogen and $R_5$ denotes methyl, ethyl, n-butyl, phenyl, 2-hydroxyethyl or 2-aminoethyl.

4. The composition as claimed in claim 1, wherein the compound of formula (I) is 2,4-diamino-5-chloro-6-n-butyloxypyrimidine 3-oxide or 2,4-diamino-5-nitro-6-n-butyloxypyrimidine 3-oxide.

5. The pharmaceutical or cosmetic composition, intended to be used in topical application, which comprises, in a physiologically acceptable medium, at least one compound as defined in claim 1.

6. The composition as claimed in claim 5, in the form of an anhydrous or aqueous, ointment, tincture, cream, pomade, powder, patch, impregnated pad, solution, emulsion, vesicular dispersion, lotion, gel, spray or suspension.

7. The composition defined in claim 5, in the form of a lotion, gel, soap, shampoo, aerosol or foam, at a concentration of between 0.01 and 5% by weight.

8. The composition as claimed in claim 5, further comprising antiseborrheic agents.

9. The composition as claimed in claim 5, further comprising agents for further improving the activity of the compounds of formula (I) for slowing down hair loss and for inducing and stimulating its growth.

10. The composition as claimed in claim 9, wherein the agents are nicotinic acid esters, steroidal or nonsteroidal antiinflammatory agents, retinoids, antibacterial agents, calcium antagonistic agents, hormones, antiandrogenic agents or hydroxyl radical scavengers.

11. The composition as claimed in claim 9, further comprising diazoxide, spiroxasone, the phospholipids, linoleic or linolenic acids, salicylic acid or its derivatives, the hydroxycarboxylic or ketocarboxylic acids, their esters, the lactones their corresponding salts, anthralin, the carotenoids, 5,8,11,14-eicosatetraynoic or 5,8,11-eicosatriynoic acids, their esters or amides.

12. The composition as claimed in claim 5, further comprising nonionic or amphoteric surface-active agents.

13. The composition as claimed in claim 5, wherein the physiologically acceptable medium consists of water, a mixture of water and one or more organic solvent(s) or of a mixture of organic solvents, the organic solvents being pharmaceutically or cosmetically acceptable.

14. The composition as claimed in claim 13, wherein the solvents are $C_1$–$C_4$ lower alcohols, alkylene glycols or mono- and dialkylene glycol alkyl ethers.

15. The composition as claimed in claim 5, wherein the physiologically acceptable medium is thickened by means of thickening and/or gelling agents and contains preserving agents, stabilizing agents, pH regulating agents, agents for modifying osmotic pressure, emulsifying agents, UV-A or UV-B filters or antioxidant agents.

16. Compounds of formula:

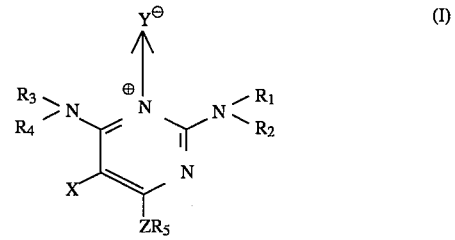

(I)

in which:

$R_1$ and $R_3$ denote a hydrogen atom;

$R_2$ and $R_4$, which are identical or different, represent a hydrogen atom or a $C_1$–$C_4$ alkyl group;

$R_5$ denotes a hydrogen atom, a $C_1$–$C_{12}$ alkyl radical, a $C_3$–$C_{12}$ alkenyl radical, a $C_3$–$C_8$ cycloalkyl radical, an aryl radical, an arylalkyl radical or a hydroxyalkyl or aminoalkyl radical in which the alkyl radical has 1 to 6 carbon atoms;

X denotes a hydrogen atom, a halogen atom, a $C_1$–$C_6$ alkyl radical, a nitro group, a benzoyloxy group or a group —$NHR_6$ in which $R_6$ denotes a hydrogen atom, an acyl radical or a $C_1$–$C_6$ alkyl radical;

Z denotes sulfur or oxygen; with the proviso that Z denotes sulfur when X denotes hydrogen or when $R_5$ denotes an aryl radical;

Y denotes oxygen or $OSO_3$;

and the addition salts with cosmetically and pharmaceutically acceptable acids; with the exception of the compounds 2,4-diamino-6-hydroxy-5-bromopyrimidine 3-oxide and 2,4-diamino-6-thiophenylpyrimidine 3-oxide and their addition salts with acids.

* * * * *